United States Patent [19]

Henrie, II

[11] Patent Number: 4,735,650
[45] Date of Patent: Apr. 5, 1988

[54] PYRIDAZINYLUREA N-OXIDE PLANT REGULATORS

[75] Inventor: Robert N. Henrie, II, East Windsor, N.J.

[73] Assignee: FMC Corporation, Philadelphia, Pa.

[21] Appl. No.: 786,272

[22] Filed: Oct. 10, 1985

[51] Int. Cl.$^4$ .................... A01N 43/58; C07D 237/12; C07D 237/20; C07D 237/22
[52] U.S. Cl. ........................ 71/92; 544/224; 544/239; 544/240; 544/241
[58] Field of Search ............... 544/224, 239, 240, 241; 71/92, 94

[56] References Cited

U.S. PATENT DOCUMENTS

| | | | |
|---|---|---|---|
| 3,330,641 | 7/1967 | Woods et al. | 71/94 |
| 3,520,886 | 7/1970 | Reicheneder et al. | 544/241 |
| 4,063,928 | 12/1977 | Johnston | 71/92 |
| 4,149,872 | 4/1979 | Pilgram | 71/94 |
| 4,193,788 | 3/1980 | Shudo et al. | 71/92 |
| 4,308,054 | 12/1981 | Isogai | 71/94 |
| 4,331,807 | 5/1982 | Okamoto et al. | 71/92 |
| 4,397,678 | 8/1983 | Okamoto et al. | 71/92 |
| 4,619,686 | 10/1986 | Abdulla et al. | 71/92 |

FOREIGN PATENT DOCUMENTS

| | | | |
|---|---|---|---|
| 0052668 | 6/1982 | European Pat. Off. | 544/224 |
| 0169051 | 1/1986 | European Pat. Off. | |
| 84/03884 | 10/1984 | PCT Int'l Appl. | 71/94 |

OTHER PUBLICATIONS

Bruce and Zwar, *Proc. Roy. Soc. B*, 165 p. 245 (1966).
Ohsawa et al. *Chem. Pharm. Bull.* 28 p. 3570 (1980).
"Plant Growth Regulators and Herbicide Antagonists'-'-Recent Advances, Edited by J. C. Johnson (1982) p. 1.
Kosary et al., *Acta Pharmaceutica Hungarica*, vol. 53, pp. 106–114, (1983).
Zupan et al., *J. Org. Chem.*, vol. 37, No. 19, pp. 2960–2963, (1972).
Isogai in *Chemical Regulation in Plants*, 17, pp. 27–43 (1982), "Shoot Formation in Response to Cytokinins in Cultured Tobacco Callus and Some Problems Associated with the Phenomenon".
Still et al. *J. Org. Chem.* 43, No. 14, pp. 2923–2925 (1978).
"Preparative Chromatography Techniques", K. Hostettmann et al., (Springer–Verlag Press, New York) pp. 41–47 (1986).
Ogata et al., *Chem. Pharm. Bull. Japan* 11, p. 29 (1963).
Itai et al., *Chem. Pharm. Bull. Japan* 10 p. 643 (1962).
Chem. Pharm. Bull., 28(12), 3570–3575 (1980)–Cas Online Prints (3) Abstract for JP 194804 (11/12/83).

*Primary Examiner*—Donald G. Daus
*Assistant Examiner*—Emily Bernhardt
*Attorney, Agent, or Firm*—Patrick C. Baker; H. Robinson Ertelt

[57] ABSTRACT

Pyridazinylurea N-oxide plant regulators of the formula

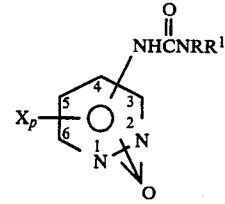

and acid addition salts thereof; wherein R is alkyl, cycloalkyl or phenyl optionally substituted with halogen; $R^1$ is hydrogen or alkyl; each X independently is halogen, alkoxy, alkylthio or alkylsulfonyl; p is 0, 1 or 2; and wherein the $NHCONRR^1$ group is bonded to the pyridazinyl ring in the 3- or 4-position; provided that (a) when X is halogen, p is 1 or 2 and the $NHCONRR^1$ group is in the 4-position, the halogen is in at least one of the 5- and 6-positions, and (b) when X is halogen, p is 1 or 2 and the $NHCONRR^1$ group is in the 3-position, the halogen is in at least one of the 4- and 5-positions.

24 Claims, No Drawings

PYRIDAZINYLUREA N-OXIDE PLANT REGULATORS

BACKGROUND OF THE INVENTION

This invention concerns certain pyridazinylurea N-oxides and their use as plant regulators.

Plant regulators are hormone-like substances which influence growth and development of plants, as inhibitors or promoters of growth. Sometimes the same compound can both inhibit and promote growth, depending upon the rate of application. Plant regulatory activity is reflected in a variety of ways, including one or more of cell enlargement, leaf and organ abscission, retardation of senescence, apical dominance, fruit set and growth, leaf growth, light response, protein synthesis, and other effects. In economic crops and ornamentals, plant regulators have enormous potential as herbicides, rooting promoters, flowering stimulants, fruit developers, and as agents to control or induce seedlessness, plant shape, and the setting, thinning and dropping of fruit. The most familiar classes of plant regulators are the auxins, gibberellins, cytokinins, abscisic acid and ethylene, but the search continues for even more active plant regulating compounds, including compounds having specific forms of regulator activity.

Representative of research efforts in the field are the compounds disclosed in U.S. Pat. Nos. 4,063,928 (substituted pyridinyloxy(thio)phenyl acetamides, ureas and urea derivatives), 4,193,788 (N-(2-chloro-4-pyridyl)ureas and thioureas), 4,308,054 (other pyridyl ureas) and 4,331,807 (N-(4-pyridazinyl)-N'-phenylureas).

SUMMARY OF THE INVENTION

A new class of plant regulating compounds has now been found. The compounds are pyridazinylurea N-oxides of the formula (I):

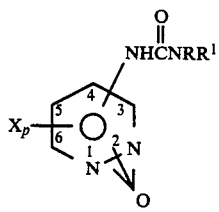

and acid addition salts thereof; wherein R is alkyl, cycloalkyl or phenyl optionally substituted with halogen; $R^1$ is halogen or alkyl; each X independently is halogen, alkoxy, alkylthio or alkylsulfonyl; p is 0, 1 or 2; and wherein the $NHCONRR^1$ group is bonded to the pyridazinyl ring in the 3- or 4-position; provided that when X is halogen, p is 1 or 2 and the $NHCONRR^1$ group is in the 4-position, the halogen is in at least one of the 5- and 6-positions, and when X is halogen, p is 1 or 2 and the $NHCONRR^1$ group is in the 3-position, the halogen is in at least one of the 4- and 5-positions.

The compounds exhibit plant regulatory activity in terms of one or more of stunting, dessication, axillary growth stimulation, nastic response, growth stimulation, defoliation, intumescence, negative root geotropism, darker green basal leaves, leaf alteration and retardation of senescenece.

DETAILED DESCRIPTION

In formula I, R, $R^1$ and X may contain any number of carbon atoms and any form of branching, for example, 1 to 20 carbon atoms or more. However, 1 to 8 carbon atoms are preferred, more preferably 1 to 4 carbon atoms in the case of all groups other than cycloalkyl, from the standpoint of ease of synthesis. The cycloalkyl group preferably will contain 3 to about 10 carbon atoms, such as cyclopentyl, cyclohexyl and cycloheptyl. "Halogen" means chloro, bromo, fluoro and iodo, preferably in that order. The phenyl group may be substituted with more than one halogen atom, either the same halogen or mixed halogens.

As indicated in formula I, the N-oxide may be in the 1- or 2-position of the pyridazinyl ring. Usually, when the $NHCONRR^1$ group is bonded to the pyridazinyl ring at the 3-position, the N-oxide will be in the 2-position, and when the $NHCONRR^1$ group is bonded to the pyridazinyl ring in the 4-position, the N-oxide group will be in the 1-position or the synthesis product will be an isomeric mixture of the 1-oxide and 2-oxide compounds. Isomeric compounds may be separated and used individually as plant regulators, or the isomeric product mixture may be employed without separation of the isomers. For conventional methods of separating the 1-oxide and 2-oxide isomers, such as column chromatography, see J. Org. Chem., 43, No. 14, 1978, 2923–2925, Chem. Pharm. Bull, Japan, 11, No. 1, 1963, 29–39, Chem. Pharm. Bull. Japan, 10, No. 7, 1962, 643–645.

When X in formula I is halogen, such as chloro, and the $NHCONRR^1$ group is in the 4-position on the pyridazinyl ring, plant regulator activity of the compounds is greater if the halogen is in the 5- and/or 6-positions on the pyridazinyl ring. Similarly, when the $NHCONRR^1$ group is in the 3-position on the pyridazinyl ring, plant regulator activity is greater if the halogen is in one or both of the 4- and 5-positions.

The acid addition salts of the compounds of formula I include organic and inorganic salts such as the hydrochlorides, sulfates, phosphates, citrates and tartrates.

Compounds of the invention include the following, including mixtures of any two of the compounds which are related as the 1-oxide and 2-oxide isomers:

N-(4-pyridazinyl-1-oxide)-N'-(1-methylethyl)urea
N-(4-pyridazinyl-2-oxide)-N'-(1-methylethyl)urea
N-(3-pyridazinyl-2-oxide)-N'-(1-methylethyl)urea
N-(3-pyridazinyl-2-oxide)-N'-phenylurea
N-(4-pyridazinyl-1-oxide)-N'-phenylurea
N-(4-pyridazinyl-2-oxide)-N'-phenylurea
N-(4-pyridazinyl-1-oxide)-N'-(3-fluorophenyl)urea
N-(4-pyridazinyl-2-oxide)-N'-(3-fluorophenyl)urea
N-(4-pyridazinyl-1-oxide)-N'-(3,5-difluorophenyl)urea
N-(4-pyridazinyl-2-oxide)-N'-(3,5-difluorophenyl)urea
N-(4-pyridazinyl-1-oxide)-N'-cyclopentylurea
N-(4-pyridazinyl-2-oxide)-N'-cyclopentylurea
N-(4-pyridazinyl-1-oxide)-N'-cycloheptylurea
N-(4-pyridazinyl-2-oxide)-N'-cycloheptylurea
N-(4-pyridazinyl-1-oxide)-N'-cyclohexylurea
N-(4-pyridazinyl-2-oxide)-N'-cyclohexylurea
N-(6-chloro-4-pyridazinyl-1-oxide)-N'-(1-methylethyl)urea
N-(6-chloro-4-pyridazinyl-2-oxide)-N'-(1-methylethyl)urea
N-(6-methoxy-4-pyridazinyl-1-oxide)-N'-(1-methylethyl)urea
N-(6-methoxy-4-pyridazinyl-2-oxide)-N'-(1-methylethyl)urea
N-(6-methylthio-4-pyridazinyl-1-oxide)-N'-(1-methylethyl)urea N-(6-methylthio-4-pyridazinyl-2-oxide)-N'-(1-methylethyl)urea N-(6-methylsulfonyl-4-pyridazinyl-1-oxide)-N'-(1-methylethyl)urea N-(6-methylsulfonyl-4-pyridazinyl-2-oxide)-N'-(1-methylethyl)urea N-(5,6-dichloro-4pyridazinyl-1-oxide)-N'-(1-methylethyl)urea N-(5,6-dichloro-4-pyridazinyl-2-oxide)-N'-(1-methylethyl)urea N-(4-pyridazinyl-1-oxide)-N'-butyl-N'-methylurea N-(4-pyridazinyl-2-oxide)-N'-butyl-N'-methylurea N-(4-pyridazinyl-1-oxide)-N'-(1,1-dimethylethyl)-N'-methylurea N-(4-pyridazinyl-2-oxide)-N'-(1,1-dimethylethyl)-N'-methylurea N-(4-pyridazinyl-1-oxide)-N'-cyclopentyl-N'-methylurea N-(4-pyridazinyl-2-oxide)-N'-cyclopentyl-N'-methylurea N-(4-pyridazinyl-1-oxide)-N'-cyclohexyl-N'-methylurea N-(4-pyridazinyl-2-oxide)-N'-cyclohexyl-N'-methylurea The compounds of formula I wherein R is other than cycloalkyl are prepared in a generally known manner by oxidizing pyridazine to the N-oxide with hydrogen peroxide, nitrating with a mixture of fuming sulfuric and nitric acids, reducing the nitro group to amino by hydrogenation over palladium on carbon, and coupling with an isocyanate (R-NCO). For preparation of compounds of formula I wherein R is cycloalkyl, the amino intermediate is reacted with phenyl chloroformate to form a phenyl N-(pyridazinyloxide)carbamate intermediate which is then reacted with a cycloalkyl amine to form the cycloalkyl product. Alternatively, an aminopyridazine intermediate is prepared by amminating a chloropyridazine and hydrogenating over palladium on carbon. The aminopyridazine is then reacted with an appropriate isocyanate (R-NCO) to form the pyridazinyl urea. The pyridazinyl urea is oxidized to the N-oxide product by reaction with m-chloroperoxybenzoic acid. Products prepared by the alternative route generally are isomeric mixtures of the 1-oxide and 2-oxide, which can be separated in a known manner, if desired. The reactions are conducted in appropriate organic solvents with appropriate pressure and temperature controls. The work-up and isolation procedures are conventional.

Further details of synthesis are given in the representative examples below. Table I lists the compounds of Examples 1-6 and provides characterizing data for the synthesis examples and other compounds of the invention.

EXAMPLE 1

Synthesis of N-(4-pyridazinyl-1-oxide)-N'-phenylurea

Step A: Pyridazine-1-oxide

With stirring, 100 ml of trifluoroacetic acid was cooled and 15.9 grams (0.20 mole) of pyridazine was added, followed by 44.6 ml (2 equiv.) of aqueous 30% hydrogen peroxide. Upon completion of addition, the reaction mixture was stirred at ambient temperature for several days until analysis of the reaction mixture by thin layer chromatography indicated that the reaction was complete. The reaction mixture was concentrated under reduced pressure to one-half volume to remove excess hydrogen peroxide. The concentrate was diluted to full volume with water and again concentrated under reduced pressure to one-half volume. The dilution-concentration procedure was repeated two additional times. The concentrate was neutralized with solid sodium bicarbonate. Sodium bisulfite was added to destroy any remaining hydrogen peroxide, then the mixture concentrated under reduced pressure to 50-75 ml in volume. The concentrate was extracted with methylene chloride using a continuous extractor. The extract was dried with sodium sulfate and filtered. The filtrate was concentrated under reduced pressure to give 12.4 grams of pyridazine-1-oxide as a low melting solid. The nmr spectrum was consistent with the proposed structure.

Step B: 4-Nitropyridazine-1-oxide

With cooling and stirring, 5.1 grams (0.053 mole) of pyridazine-1-oxide was dissolved in 50 ml of fuming sulfuric acid. To this was added 8.83 ml of fuming nitric acid. Upon completion of addition the reaction mixture was warmed to 130°-135° C. where it stirred for two hours. Analysis of the reaction mixture by thin layer chromatography (TLC) indicated the reaction was not complete. The reaction mixture was allowed to cool to ambient temperature where it stood for 16 hours. An additional 1.3 ml of fuming nitric acid was added and the reaction mixture was heated to 130°-135° C. where it stirred for 4 hours. Analysis of the reaction mixture by TLC indicated the reaction still had not gone to completion. An additional 1.3 ml of fuming nitric acid was added to the reaction mixture, which was stirred an additional 4 hours at 130°-135° C. The reaction mixture was poured into ice-water where it stood for several hours. The pH of the mixture was adjusted to near 7 with sodium bicarbonate, then the mixture was extracted with methylene chloride using a continuous extractor. The extract was dried with sodium sulfate and filtered. The filtrate was subjected to column chromatography on silica gel using 10% acetone in methylene chloride as eluent. The appropriate fractions were combined and concentrated under reduced pressure to give 1.1 grams of 4-nitropyridazine-1-oxide, m.p. 149°-151.5° C.

Step C: 4-Aminopyridazine-1-oxide

Using a Parr hydrogenator, a solution of 3.1 grams (0.022 mole) of 4-nitropyridazine-1-oxide (a combination of several runs as described in Step B) in 100 ml of methanol was hydrogenated in the presence of 1.0 gram of 10% palladium on charcoal. Upon completion of the hydrogenation the reaction mixture was filtered, and the filter cake washed repeatedly with methanol. The combined filtrate and washes were concentrated under reduced pressure to give a solid. The solid was dried at 50° C. and recrystallized from ethyl acetate to give 2.2 grams of 4-aminopyridazine-1-oxide; m.p. 210°-212° C. The nmr spectra were consistent with the proposed structure.

Step D: N-(4-pyridazinyl-1-oxide)-N-phenylurea

To a stirred solution of 0.5 gram (0.0045 mole) of 4-aminopyridazine-1-oxide in 25 ml of dimethylformamide was added 0.14 gram (0.0013 mole) of 1,4-diazabicyclo[2.2.2]octane, followed by 0.58 ml (0.0054 mole) of phenyl isocyanate. The reaction mixture was stirred at ambient temperature for 15 hours, then at 60° C. for 6 hours. The majority of the dimethylformamide was removed under reduced pressure and the residue slurried in water. The resultant solid was collected by filtration and washed with water. The solid was recrystallized from 60 ml of glacial acetic acid to give 0.55 gram of N-(4-pyridazine-1-oxide)-N'-phenylurea; m.p. 264°–265° C.; dec. The nmr and the ir spectra were consistent with the proposed structure.

EXAMPLE 2

Synthesis of N-(4-pyridazinyl-1-oxide)-N'-(3,5-difluorophenyl)urea

Step A: 4-Aminopyridazine

A solution of 10.1 grams (0.055 mole) of 3,4,5-trichloropyridazine in 100 ml of absolute ethanol, in a 200 ml pressure bottle, was cooled to 0° C. and saturated with ammonia gas. The bottle was sealed and the reaction mixture stirred at ambient temperature for 4 days. The reaction mixture was purged with nitrogen for 2 hours then filtered to remove ammonium chloride. The filter cake was washed with anhydrous ethanol. The filtrate and washed were placed in a Parr hydrogenation bottle and 5.2 grams (0.13 mole) of sodium hydroxide and 0.6 gram of 10% palladium on charcoal were added. The volume of the mixture was brought to 200 ml with absolute ethanol. The mixture was hydrogenated for 4 hours using a Parr hydrogenator, during which time the theoretical amount of hydrogen was taken up. The hydrogenation bottle was purged with nitrogen and the reaction mixture was filtered through diatomaceous earth. The filtrate was concentrated under reduced pressure to a residue. The residue was dried under reduced pressure at ambient temperature for several hours. The residue was triturated with 250 ml of ethyl acetate, and the mixture allowed to stand for 7 days under anhydrous conditions. The mixture was filtered to collect a solid. The solid was dried under reduced pressure at 40° C. to give 3.9 grams of 4-aminopyridazine. The nmr spectrum was consistent with the proposed structure.

Step B: N-(4-pyridazinyl)-N'-(3,5-difluorophenyl)urea

To a stirred solution of 2.7 grams (0.021 mole) of 3,5-difluoroaniline in 100 ml of dioxane was added via syringe 1.5 ml (0.013 mole ) of trichloromethyl chloroformate. The reaction mixture was heated under reflux for 18 hours, cooled to ambient temperature, and 2.0 grams (0.021 mole) of 4-aminopyridazine and 7.01 ml (0.05 mole) of triethylamine were added. The reaction mixture was heated at 50° C. for one day, cooled to ambient temperature and filtered. The filter cake was washed with dioxane and dried. The solid was slurried in hot water for one hour. The mixture was filtered and the filter cake dried to give 4.1 grams of N-(4-pyridazinyl)-N'-(3,5-difluorophenyl)urea; m.p. 272°–273° C. The nmr spectrum was consistent with the proposed structure.

Step C: N-(4-pyridazinyl-1-oxide)-N'-(3,5-difluorophenyl)urea

To a stirred solution of 3.4 grams (0.014 mole) of N-(4-pyridazinyl)-N'-(3,5-difluorophenyl)urea in 450 ml of triethylphosphate, at 45° C., was added 3.6 grams (0.018 mole) of m-chloroperoxybenzoic acid. The reaction mixture was warmed to 50° C. where it stirred for two days. A solid precipitate was collected by filtration and dried to give 0.5 gram of N-(4-pyridazinyl-1-oxide)-N'-(3,5-difluorophenyl)urea; m.p. 264°–265° C. The nmr spectrum indicated the product was 100% 1-oxide.

EXAMPLE 3

Synthesis of an isomeric mixture of N-(4-pyridazinyl-1-oxide)-N'-phenylurea and N-(4-pyridazinyl-2-oxide)-N'-phenylurea This compound was prepared in a manner analogous to Example 2, Step C using 1.4 grams (0.007 mole) of N-(4-pyridazinyl)-N'-phenylurea (prepared as in Example 1, Step D) and 2.7 grams (0.016 mole) of m-chloroperoxybenzoic acid in 150 ml of triethylphosphate. The yield of product was 0.87 gram as a solid, m.p. 253°–255° C., dec. Analysis of the nmr spectrum from the solid indicated it to be a mixture of 70% N-(4-pyridazinyl-1-oxide)-N'-phenylurea and 30% N-(4-pyridazinyl-2-oxide)-N'-phenylurea.

EXAMPLE 4

Synthesis of N-(3-pyridazinyl-2-oxide)-N'-(1-methylethyl)urea

Step A: 3-Aminopyridazine

This compound was prepared in a manner analogous to Example 2, Step A by the hydrogenation of 9.5 grams (0.073 mole) of commercially available 3-amino-6-chloropyridazine, in the presence of 3.7 grams (0.09 mole) of sodium hydroxide and 0.8 gram of 10% palladium on charcoal in ethanol. The yield of 3-aminopyridazine was 7.5 grams as a solid.

Step B: N-(3-Pyridazinyl)-N'-(1-methylethyl)urea

This compound was prepared in a manner analogous to Example 1, Step D using 2.9 grams (0.031 mole) of 3-aminopyridazine, 3.9 ml (0.04 mole) of 1-methylethyl isocyanate, and 0.75 gram (0.007 mole) of 1,4-diazabicyclo[2.2.2]octane in 50 ml of dimethylformamide. The yield of N-(3-pyridazinyl)-N'-(1-methylethyl)urea was 1.2 grams as a solid. The nmr spectrum was consistent with the proposed structure. The reaction was repeated several times.

Step C: N-(3-Pyridazinyl-2-oxide)-N'-(1-methylethyl)urea

This compound was prepared in a manner analogous to Example 2, Step C using 1.8 grams (0.01 mole) of N-(3-pyridazinyl)-N'-(1-methylethyl)urea and 2.2 grams (0.013 mole) of m-chloroperoxybenzoic acid in 250 ml of triethylphosphate. The yield of product was 0.46 gram as a solid, m.p. 201°–203° C., dec. Analysis of the nmr spectrum from the solid indicated it to be 100% N-(3-pyridazinyl-2-oxide)-N'-(1-methylethyl)urea.

EXAMPLE 5

Synthesis of an isomeric mixture of N-(4-pyridazinyl-1-oxide)-N'-cyclopentylurea and N-(4-pyridazinyl-2-oxide)-N'-cyclopentylurea Step A: Phenyl N-(4-pyridazinyl)carbamate A stirred suspension of 2.6 grams (0.027 mole) of 4-aminopyridazine (prepared as in Example 2, Step A) in 100 ml of tetrahydrofuran was cooled to 0° C. and 4.6 ml (0.033 mole) of triethylamine was added in one portion. A solution of 4.1 ml (0.033 mole) of phenyl chloroformate in tetrahydrofuran was added dropwise during a 30 minute period. Upon completion of addition the reaction mixture was allowed to warm to ambient temperature where it stirred for three days. The reaction mixture was concentrated for three days. The reaction mixture was concentrated under reduced pressure to a residue. The residue was taken up in 500 ml of chloroform and filtered to collect 1.9 grams of phenyl N-(4-pyridazinyl)carbamate; m.p. 184°–185° C. The filtrate was washed with water then dried with magnesium sulfate. The mixture was filtered and the filtrate placed on a column of silica gel. Further elution was accomplished using 10% methanol in methylene chloride. The appropriate fractions were combined and concentrated under reduced pressure to yield an additional 1.8 grams of phenyl N-(4-pyridazinyl)carbamate. The nmr spectra were consistent with the proposed structure. The reaction was repeated several times.

Step B: N-(4-pyridazinyl)-N'-cyclopentylurea

A stirred solution of 2.0 grams (0.009 mole) of phenyl N-(4-pyridazinyl)carbamate and 1.0 ml of cyclopentylamine in tetrahydrofuran was heated under reflux for 18 hours. The reaction mixture was filtered and the filtrate concentrated under reduced pressure to a residue. The residue was purified by column chromatography on silica gel. Elution was accomplished with 10% methanol in methylene chloride. The appropriate fractions were combined and concentrated under reduced pressure to yield 0.2 gram of N-(4-pyridazinyl)-N'-cyclopentylurea. This material were combined with the identical product from a previous reaction to yield 0.5 gram; m.p. 192°–195° C. dec. The nmr spectrum was consistent with the proposed structure. The reaction was repeated several times.

Step C: Isomeric mixture

To a stirred suspension of 1.3 grams (0.006 mole) of N-(4-pyridazinyl)-N'-cyclopentylurea in 150 ml of 25% methanol and ethyl acetate was added 1.5 grams (0.008 mole) m-chloroperoxybenzoic acid in one portion. The reaction mixture was heated to 45°–50° C. and stirred at this temperature for two days. The reaction mixture was filtered and the filter cake dried to yield a solid; m.p. 129°–131° C., dec. then 190°–193° C., dec. Analysis of the nmr spectrum of the solid indicated it to be a mixture of 62.5% N-(4-pyridazinyl-1-oxide)-N'-cyclopentylurea and 37.5% N-(4-pyridazinyl-2-oxide)-N-cyclopentylurea.

EXAMPLE 6

Synthesis of an isomeric mixture of N-(4-pyridazinyl-1-oxide)-N'-cycloheptylurea and N-(4-pyridazinyl-2-oxide)-N'-cycloheptylurea

Step A: N-(4-pyridazinyl)-N'-cycloheptylurea

This compound was prepared in the manner of Example 5, Step B, using 4.0 grams (0.019 mole) of phenyl N-(4-pyridazinyl)carbamate and 2.1 grams (0.019 mole) of cycloheptylamine in tetrahydrofuran. The yield of N-(4-pyridazinyl)-N'-cycloheptylurea was 2.0 grams; m.p. 226°–228° C. The nmr spectrum was consistent with the proposed structure. The reaction was repeated several times.

Step B: Isomeric mixture

This product was prepared in the manner of Example 5, Step C, using 1.4 grams (0.006 mole) of N-(4-pyridazinyl)-N'-cycloheptylurea and 1.6 grams (0.008 mole) of m-chloroperoxybenzoic acid in 150 ml of 25% methanol and ethyl acetate. The yield of product was 0.9 gram as a solid; m.p. 214°–218° C., dec., then 233°–235° C., dec. Analysis of the nmr spectrum of the solid indicated it to be a mixture of 66.7% N-(4-pyridazinyl-1-oxide)-N'-cycloheptylurea and 33.3% N-(4-pyridazinyl-2-oxide)-N'-cycloheptylurea.

TABLE I

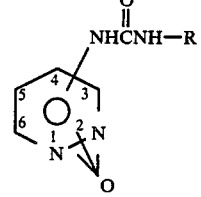

| Example No. | R | Urea Group Position | Ratio of 1:2 N—oxides | Empirical formula | Melting point, °C. dec. |
|---|---|---|---|---|---|
| 1 | phenyl | 4 | 100:0 | $C_{11}H_{10}N_4O_2$ | 264–265 |
| 2 | 3,5-difluorophenyl | 4 | 100:0 | $C_{11}H_8F_2N_4O_2$ | 264–265 |
| 3 | phenyl | 4 | 70:30 | $C_{11}H_{10}N_4O_2$ | 253–255 |
| 4 | —CH(CH$_3$)$_2$ | 3 | 0:100 | $C_8H_{12}N_4O_2$ | 201–203 |
| 5 | cyclopentyl | 4 | 62.5:37.5 | | |
| 6 | cycloheptyl | 4 | 66.7:33.3 | | |
| 7 | —CH(CH$_3$)$_2$ | 4 | 41:59 | $C_8H_{12}N_4O_2$ | 208–215 |
| 8 | phenyl | 3 | 0:100 | $C_{11}H_{12}N_4O_2$ | 226–228 |
| 9 | 3-fluorophenyl | 4 | 100:0 | $C_{11}H_9FN_4O_2$ | 276.5–277.5 |
| 10 | 3-fluorophenyl | 4 | 66:34 | $C_{11}H_9FN_4O_2$ | 258–260 |

Plant Regulator Utility

The pyridazinylurea N-oxides of the invention exhibit various forms of plant regulator activity when tested in vitro and in whole plant assays as described more particularly hereinbelow. Briefly, such activity is apparent in preemergence and postemergence plant response screens on a variety of plants, particularly soybean and cotton, where morphological responses include stunting, axillary growth stimulation, nastic response, defoliation, darker green basal leaves, and some herbicidal activity. In antisenescence assays, compounds of the invention cause retention of chlorophyll in excised wheat leaves and in soybean leaves and pods, while reducing abscission, thus indicating ability to retard senescence.

The plant regulators of this invention are effectively employed as plant regulators in a number of broadleafed and grain crops, for example, soybean, lima bean, wheat, rice, corn, sorghum, and cotton, and turf grasses.

The plant regulator compounds, like most agricultural chemicals, are generally not applied full strength, but are formulated with agriculturally acceptable carriers or extenders (diluents) normally employed for facilitating the dispersion of active ingredients and various additives, and optionally with other active ingredients, recognizing that the formulation and mode of application of the active component may affect the activity of the material. The present compounds may be applied, for example, as powders or liquids, the choice of application varying with the plant species and environmental factors present at the particular locus of application. Thus, the compounds may be formulated as emulsifiable concentrates, wettable powders, flowable formulations, solutions, dispersions, suspensions and the like.

A typical formulation may vary widely in concentration of the active ingredient depending on the particular agent used, the additives and carriers used, other active ingredients, and the desired mode of application. With due consideration of these factors, the active ingredient of a typical formulation may, for example, be suitably present at a concentration of from about 0.5% up to about 99.5% by weight of the formulation. Substantially inactive ingredients such as adjuvants, diluents, and carriers may comprise from about 99.5% by weight to as low as about 0.5% by weight of the formulation. Surface active agents, if employed in the formulation, may be present at various concentrations, suitably in the range of 1 to 30% by weight. Provided below is a general description of representative formulations which may be employed for dispersion of the plant regulators of the present invention.

Emulsifiable concentrates (EC's) are homogeneous liquid compositions, usually containing the active ingredient dissolved in a liquid carrier. Commonly used liquid carriers include xylene, heavy aromatic naphthas, isophorone, and other nonvolatile or slightly volatile organic solvents. For application, these concentrates are dispersed in water, or other liquid vehicle, forming an emulsion, and are normally applied as a spray to the area to be treated. The concentration of the essential active ingredient in EC's may vary according to the manner in which the composition is to be applied, but, in general, is in the range of 0.5 to 95%, frequently 10 to 80%, by weight of active ingredient, with the remaining 99.5% to 5% being surfactant and liquid carrier.

The following are specific examples of emulsifiable concentrate formulations suitable for use in the present invention:

|  | % by Wt. |
|---|---|
| Formulation 1: | |
| Active ingredient | 53.01 |
| Blend of alkylbenzenesulfonate salt and polyoxyethylene ethers | 6.00 |
| Epoxidized soybean oil | 1.00 |
| Xylene | 39.99 |
| Total | 100.00 |
| Formulation 2: | |
| Active ingredient | 10.00 |
| Blend of alkylbenzenesulfonate salt and polyoxyethylene ethers | 4.00 |
| Xylene | 86.99 |
| Total | 100.00 |

Wettable powders, also useful formulations for plant regulators, are in the form of finely divided particles which disperse readily in water or other liquid vehicles. The wettable powder is ultimately applied to the plant as a dry dust or a dispersion in water or other liquid. Typical carriers for wettable powders include fuller's earth, kaolin clays, silicas, and other highly absorbent or adsorbent inorganic diluents. The concentration of active ingredient in wettable powders is dependent upon physical properties of the active ingredient and the absorbency characteristics of the carrier. Liquids and low melting solids (mp<100° C.) are suitably formulated in the concentration range of 5 to 50% by weight, usually from 10 to 30%; high melting solids (mp>100° C.) being formulated in the range of 5 to 95% by weight, usually 50 to 85%. An agriculturally acceptable carrier or diluent, frequently including a small amount of a surfactant to facilitate wetting, dispersion and suspension, accounts for the balance of the formulation.

The following are specific examples of wettable powder formulations suitable for use in the present invention:

|  | % by Wt. |
|---|---|
| Formulation 3: | |
| Active ingredient | 40.00 |
| Sodium ligninsulfonate/sodium alkylnaphthalenesulfonate | 4.00 |
| Attapulite clay | 56.00 |
| Total | 100.00 |
| Formulation 4: | |
| Active ingredient | 90.00 |
| Dioctyl sodium sulfosuccinate | 0.10 |
| Synthetic fine silica | 9.90 |
| Total | 100.00 |
| Formulation 5: | |
| Active ingredient | 20.00 |
| Sodium alkylnaphthalenesulfonate | 4.00 |
| Sodium ligninsulfonate | |
| Attapulite clay | 75.00 |
| Total | 100.00 |
| Formulation 6: | |
| Active ingredient | 25.00 |
| Base: | 75.00 |
| 96% hydrated aluminum magnesium silicate 2% powdered sodium ligninsulfonate 2% powdered anionic sodium alkyl-naphthalenesulfonate | |
| Total | 100.00 |

Flowable formulations are similar to EC's except that the active ingredient is suspended in a liquid carrier, generally water. Flowables, like EC's, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations suitable for use in the present invention:

|  | % by Wt. |
|---|---|
| Formulation 7: | |
| Active ingredient | 46.00 |
| Colloidal mangesium aluminum silicate | 0.40 |
| Sodium alkylnaphthalenesulfonate | 2.00 |
| Paraformaldehyde | 0.10 |
| Water | 41.42 |
| Propylene glycol | 7.50 |
| Acetylinic alcohols | 2.50 |

|                                | % by Wt. |
|--------------------------------|----------|
| Xanthan gum                    | 0.08     |
| Total                          | 100.00   |
| Formulation 8:             |          |
| Active ingredient              | 45.00    |
| Water                          | 48.50    |
| Purified smectite clay         | 2.00     |
| Xanthan gum                    | 0.50     |
| Sodium alkylnaphthalenesulfonate | 1.00   |
| Acetylinic alcohols            | 3.00     |
| Total                          | 100.00   |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively non-volatile solvent such as water, corn oil, kerosene, propylene glycol, or other suitable solvents. This type of formulation is particularly useful for ultra low volume application.

The following illustrate specific suspensions which are suitable for use in the present invention:

|                                | % by Wt. |
|--------------------------------|----------|
| Formulation 9:             |          |
| Oil Suspension:            |          |
| Active ingedient               | 25.00    |
| Polyoxyethylene sorbitol hexaoleate | 5.00 |
| Highly aliphatic hydrocarbon oil | 70.00  |
| Total                          | 100.00   |
| Formulation 10:            |          |
| Aqueous Suspension:        |          |
| Active ingredient              | 40.00    |
| Polyacrylic acid thickener     | 0.30     |
| Dodecylphenol polyethylene glycol ether | 0.50 |
| Disodium phosphate             | 1.00     |
| Monosodium phosphate           | 0.50     |
| Polyvinyl alcohol              | 1.00     |
| Water                          | 56.70    |
| Total                          | 100.00   |

The concentration of the compound in use dilution is normally in the range of about 2% to about 0.1%. Many variations of spraying and dusting compositions in the art may be used by substituting or adding a compound of this invention into compositions known or apparent to the art.

The compositions may be formulated and applied with other suitable active ingredients, including nematicides, insecticides, acaricides, fungicides, other plant regulators, herbicides, fertilizers, etc.

In applying the foregoing chemicals, an effective growth regulating amount of the active ingredient must be applied. While the application rate will vary widely depending on the choice of compound, the formulation and mode of application, the plant species being treated and the planting density, a suitable use rate may be in the range of 0.01 to 10 kg/hectare, preferably 0.05 to about 5 kg/hectare.

The compounds of the invention were tested for plant regulator activity, first in a whole plant response screen and then in excised wheat leaf and soybean whole plant antisenescence tests. Compounds tested are identified as follows:

TABLE II

| Cpd. No. | Test Compounds |
|----------|----------------|
| 1 | Isomeric mixture (41:59 by weight) of N—(4-pyridazinyl-1-oxide)-N'—(1-methylethyl)urea and N—(4-pyridazinyl-2-oxide)-N'—(1-methylethyl)urea |
| 2 | N—(3-pyridazinyl-2-oxide)-N'—1-methylethyl)urea |
| 3 | N—(3-pyridazinyl-2-oxide)-N'—phenylurea |
| 4 | N—(4-pyridazinyl-1-oxide)-N'—phenylurea |
| 5 | Isomeric mixture (70:30 by weight) of N—(4-pyridazinyl-1-oxide)-N'—phenylurea and N—(4-pyridazinyl-2-oxide)-N'—phenylurea |
| 6 | N—(4-pyridazinyl-1-oxide)-N'—(3-fluorophenyl)urea |
| 7 | Isomeric mixture (66:34 by weight) of N—(4-pyridazinyl-1-oxide)-N'—(3-fluorophenyl)urea and N—(4-pyridazinyl-2-oxide)-N'—(3-fluorophenyl)urea |
| 8 | N—(4-pyridazinyl-1-oxide)-N'—(3,5-difluorophenyl)urea |

Plant Response Screen

In this assay the test compounds are applied as water-acetone (1:1) solutions, containing 0.5% v/v sorbitan monolaurate solubilizer, at a rate equivalent to 8.0 kg/ha, preemergently to planted seeds of test plants and postemergently to foliage of test plants. The test plants were soybean, cotton, corn, wheat, field bindweed, morningglory, velvetleaf, barnyardgrass, green foxtail and johnsongrass.

All of the test compounds exhibited various forms and degrees of plant regulator activity although not against all of the plants in each case. Generally, the test compounds were more active when applied postemergently. The soybean and cotton plants were particularly responsive as evidenced by stunting, axillary growth stimulation, nastic response, defoliation, and darker green basal leaves. Some herbicidal activity was exhibited at the exceptionally high application rate of the test.

Wheat Leaf Antisenescence

1. Initial Test

In this test leaves were excised from wheat seedlings (*Triticum aestivum* cv. Prodox), weighed and placed in vials containing solutions of test compound in water-acetone (1:1) at concentrations of 25 ppm and 2.5 ppm. Wheat leaves were similarly placed in vials containing only deionized water, as controls. After four days of incubation at 30° C. in the dark, the test vials were examined visually and given a numeric rating of 0 (color similar to color of the leaves in the control vials) or 1 (more green than the leaves in the control vials). The control leaves had yellowed, indicating loss of chlorophyll. The test results, set forth in Table III below, show that compounds 1, 5 and 8 caused retention of chlorophyll at 25 ppm and 2.5 ppm as compared with the control. The apparent inactivity of compound 7 is believed to be caused by its limited solubility in the water-acetone test solvent.

TABLE III

| Compound No. | Chlorophyll Retention Concentration (ppm) | Visual Rating |
| --- | --- | --- |
| 1 | 25 | 1 |
|  | 2.5 | 1 |
| 5 | 25 | 1 |
|  | 2.5 | 1 |
| 7 | 25 | 0 |
|  | 2.5 | 0 |
| 8 | 25 | 1 |
|  | 2.5 | 1 |

2. Chlorophyll Retention—Senescence Inhibition ($SI_{50}$)

Compounds of the invention were tested for their ability to retain the chlorophyll in freshly excised wheat leaves as compared with frozen wheat leaf controls which, theoretically, retain 100% of their chlorophyll. In the test, excised wheat leaves were weighed and placed in vials of water-acetone (1:1) solutions of test compounds at concentrations ranging from $10^{-5}$ to $10^{-9}$ molar. Vials containing the leaves in water alone were used as controls. After 4 days incubation at 30° C. in the dark, the chlorophyll content of the excised leaves was determined by extracting the leaves with methanol or other solvent. The absorbances of the chlorophyll-containing extracts were determined spectrophotometrically at 652 nm and converted to micrograms and chlorophyll/gram of fresh leaf weight for test vials and controls by the formula $$\frac{A\ 652\ nm}{g\ fresh\ weight} \times 299 = \mu g\ chlorophyll/g\ fresh\ weight$$

The calculated results were then divided by the micrograms of chlorophyll/gram fresh weight of the frozen leaf control and the result multiplied by 100 to give percent of chlorophyll retained as compared with the frozen wheat leaf control. The percent chlorophyll retained in the wheat leaves by the various concentrations of test chemical was plotted against the negative log of the concentration. From the resulting graph, the negative log of the concentration that would retain 50% of the chlorophyll ($SI_{50}$) was determined. The greater the $SI_{50}$ value, the more active the test chemical as a senescence inhibitor.

The results are given in Table IV for averages of three replicates from which it will be seen that all of the test compounds caused some retention of chlorophyll. Compounds 4, 5, and 7 have $SI_{50}$ values of 6.7, 6.9 and 7.4, respectively, making them the most active compounds of the test. By comparison, the $SI_{50}$ value of the unoxidized form of compounds 4 and 5 is 4.8, and the $SI_{50}$ value of the unoxidized form of compound 7 is 5.2. Furthermore, since $SI_{50}$ is the negative log of the concentration of a test compound that would retain 50% of the chlorophyll, the concentrations of compounds 4, 5, and 7 required to retain 50% of the chlorophyll are approximately 100 times less than the concentrations of the corresponding unoxidized forms needed to retain 50% of the chlorophyll. Accordingly, compounds 4, 5, and 7 are deemed 100 times more active than their unoxidized forms.

TABLE V

| Wheatleaf Chlorophyll Retention - $SI_{50}$ Values | | | | |
| --- | --- | --- | --- | --- |
| Cmpd. No. | Molar Conc'n | g Chlorophyll/g Fresh Weight | Percent Chlorophyll Retained as Compared to the Frozen Wheat Leaf Check | $SI_{50}$ |
| 1 | $10^{-5}$ | 1076.0 | 76.0* | 5.2 |
|  | $10^{-6}$ | 427.1 | 30.2* |  |
|  | $10^{-7}$ | 372.5 | 26.3 |  |
|  | $10^{-8}$ | 268.7 | 19.0 |  |
| 4 | $10^{-5}$ | 1039.7 | 67.0* | 6.7 |
|  | $10^{-6}$ | 1204.0 | 77.6* |  |
|  | $10^{-7}$ | 747.1 | 48.1* |  |
|  | $10^{-8}$ | 384.1 | 24.7 |  |
| 5 | $10^{-5}$ | 973.3 | 62.7* | 6.9 |
|  | $10^{-6}$ | 1113.2 | 71.7* |  |
|  | $10^{-7}$ | 868.4 | 55.9* |  |
|  | $10^{-8}$ | 437.8 | 28.2 |  |
| 6 | $10^{-5}$ | 1133.2 | 73.0* | 4.8 |
|  | $10^{-6}$ | 1032.1 | 66.5* |  |
|  | $10^{-7}$ | 862.4 | 55.6* |  |
|  | $10^{-8}$ | 372.7 | 24.0 |  |
| 7 | $10^{-5}$ | 1264.1 | 81.4* | 7.4 |
|  | $10^{-6}$ | 1092.5 | 70.4* |  |
|  | $10^{-7}$ | 930.2 | 59.9* |  |
|  | $10^{-8}$ | 663.1 | 42.7* |  |
| 8 | $10^{-5}$ | 1257.2 | 69.9* | 7.1 |
|  | $10^{-6}$ | 1169.6 | 65.0* |  |
|  | $10^{-7}$ | 794.7 | 44.2* |  |
|  | $10^{-8}$ | 366.5 | 20.4* |  |
| Frozen Wheat Leaf Check |  |  | 100.0 |  |
| Water Control |  |  | 22.0 |  |

*Treatments significantly different from water control.

Soybean Utility Test

Compounds of the invention were sprayed onto the foliage of soybean test plants at rates of 2.0, 0.50, and 0.125 kg/ha. The test compounds were sprayed as water-acetone (1:1) solutions containing 2% sorbitan monolaurate emulsifier. The soybean test plants were at the beginning seed stage at the time of spraying.

Approximately 15 days post-treatment, the leaves and pods and the soybean test plants were inspected for senescence. Leaf and pod senescence was measured using a rating scale of 0-5, 0 indicating leaf and pod abscission and 5 being 100% green leaves and pods. The soybean test plants were inspected periodically up to 43 days. At each inspection the leaf and pod senescence was measured using the aforementioned rating. Graphs were prepared for each test chemical in which the mean leaf senescence ratings were plotted against the corresponding days post-treatment. A second set of graphs was prepared in which the mean pod senescence ratings were plotted against the corresponding days post-treatment. Leaf and pod senescence ratings vs the corresponding days post-treatment for the untreated control were plotted on these same graphs. Using the graphs, the number of the days delay in reaching 50% leaf senescence (leaf senescence rating=2.5) for each test chemical, as compared to the untreated control, was determined. The process was repeated with the mean pod senescence ratings to determine the number of days delay in reaching 50% pod senescence (2.5) for each test chemical.

Table V gives the results from which it will be seen that compounds 4, 5 and 6 delayed both leaf and pod senescence. Compound 5 appeared to be the most active, delaying leaf and pod senescence by 12 days and 6 days, respectively.

TABLE V

Leaf and Pod Senescence of Soybean Test Plants Treated at the Beginnning Seed Stage

| Cmpd No. | Rate of Application | Leaf Senescence Ratings Days Post-Treatment | | | | | | | | |
|---|---|---|---|---|---|---|---|---|---|---|
| | | 15 | 21 | 22 | 29 | 31 | 35 | 36 | 42 | 43 |
| 4 | 2.0 kg/ha | | | | 4.8 | | 4.0 | | 1.2 | |
| | 0.5 | | | | 4.8 | | 4.0 | | 1.2 | |
| | 0.125 | | | | 4.8 | | 3.6 | | 1.0 | |
| Untreated check | | | | | 4.0 | | 2.4 | | 1.0 | |
| 5 | 2.0 | 4.4 | | 3.4 | 3.4 | | | | 2.2 | 1.2 |
| | 0.5 | 4.6 | | 4.0 | 3.8 | | | | 2.4 | 1.6 |
| | 0.125 | 4.6 | | 3.8 | 3.4 | | | | 2.0 | 1.2 |
| Untreated check | | 5.0 | | 3.6 | 1.6 | | | | 1.2 | 1.0 |
| 6 | 2.0 | | 4.4 | | | 2.6 | 1.2 | | 0.0 | |
| | 0.5 | | 4.2 | | | 2.2 | 1.0 | | 0.0 | |
| | 0.125 | | 4.0 | | | 2.6 | 1.2 | | 0.0 | |
| Untreated check | | | 3.8 | | | 1.6 | 1.0 | | 0.0 | |

| Cmpd No. | Rate of Application | Pod Senescence Rating Days Post-Treatment | | | | | | | | | Days Senescence Compared to the Untreated check | |
|---|---|---|---|---|---|---|---|---|---|---|---|---|
| | | 15 | 21 | 22 | 29 | 31 | 35 | 36 | 42 | 43 | Leaf | Pod |
| 4 | 2.0 kg/ha | | | | 5.0 | | 3.6 | | 1.0 | | | |
| | 0.5 | | | | 5.0 | | 4.0 | | 1.0 | | 7 | 6 |
| | 0.125 | | | | 4.8 | | 3.6 | | 1.0 | | | |
| Untreated check | | | | | 4.0 | | 2.2 | | 1.0 | | | |
| 5 | 2.0 | 4.0 | | 3.2 | 3.0 | | | 1.2 | | 1.0 | | |
| | 0.5 | 4.0 | | 3.2 | 2.4 | | | 1.2 | | 1.0 | 12 | 6 |
| | 0.125 | 4.0 | | 2.6 | 2.4 | | | 1.2 | | 1.0 | | |
| Untreated check | | 4.0 | | 2.0 | 1.0 | | | 1.0 | | 1.0 | | |
| 6 | 2.0 | | 5.0 | | 2.4 | 1. | | 1.0 | | | 4 | 2 |
| | 0.5 | | 4.8 | | 2.2 | 1.2 | | 1.0 | | | | |
| | 0.125 | | 5.0 | | 2.6 | 1.2 | | 1.0 | | | 4 | 3 |
| Untreated check | | | 4.6 | | 1.8 | 1.0 | | 1.0 | | | | |

I claim:

1. Pyridazinylurea N-oxide compounds of the formula:

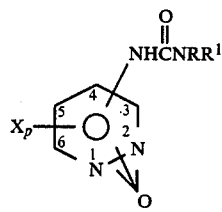

and acid addition salts thereof; wherein R is alkyl($C_1$–$C_8$), cycloalkyl($C_3$–$C_{10}$) or phenyl optionally substituted with 1 or 2 halogen atoms; $R^1$ is hydrogen or alkyl($C_1$–$C_8$); each X independently is halogen, alkoxy($C_1$–$C_8$), alkyl($C_1$–$C_8$)thio or alkyl($C_1$–$C_8$)sulfonyl; p is 0, 1 or 2; and wherein the NHCONRR$^1$ group is bonded to the pyridazinyl ring in the 4-position; provided that when X is halogen, the halogen is in at least one of the 5- and 6-positions.

2. Compounds of claim 1 wherein the N-oxide group is in the 1-position.

3. A composition comprising an isomeric mixture of (a) compounds of claim 1 wherein the N-oxide group is in the 1-position, and (b) compounds of claim 1 wherein the N-oxide group is in the 2-position.

4. A compound of claim 1 which is N-(4-pyridazinyl-2-oxide)-N'-(1-methylethyl)urea.

5. A compound of claim 1 which is N-(4-pyridazinyl-1-oxide)-N'-(1-methylethyl)urea.

6. A compound of claim 1 which is N-(4-pyridazinyl-1-oxide)-N'-phenylurea.

7. A compound of claim 1 which is N-(4-pyridazinyl-1-oxide)-N'-(3-fluorophenyl)urea.

8. A compound of claim 1 which is N-(4-pyridazinyl-2-oxide)-N'-(3-fluorophenyl)urea.

9. A compound of claim 1 which is N-(4-pyridazinyl-1-oxide)-N'-(3,5-difluorophenyl)urea.

10. A compound of claim 1 which is N-(4-pyridazinyl-2-oxide)-N'-(3,5-difluorophenyl)urea.

11. A composition of claim 3 wherein isomer (a) is N-(4-pyridazinyl-1-oxide)-N'-(1-methylethyl)urea, and isomer (b) is N-(4-pyridazinyl-2-oxide)-N'-(1-methylethyl)urea.

12. A composition of claim 3 wherein isomer (a) is N-(4-pyridazinyl-1-oxide)-N'-phenylurea, and isomer (b) is N-(4-pyridazinyl-2-oxide)-N'-phenylurea.

13. A composition of claim 3 wherein isomer (a) is N-(4-pyridazinyl-1-oxide)-N'-(3-fluorophenyl)urea, and isomer (b) is N-(4-pyridazinyl-2-oxide)-N'-(3-fluorophenyl)urea.

14. A plant growth regulator composition comprising a plant regulating amount of a compound of claim 1 in admixture with an agriculturally acceptable carrier or extender.

15. A method of retarding senescence in soybean plants which comprises applying to the plant a plant regulating amount of a compound of claim 1.

16. A method of improving leaf abscission of cotton plants for harvesting which comprises applying to the plants a defoliating amount of a compound of claim 1.

17. A method of retarding senescence in soybean plants which comprises applying to the plant a plant regulating amount of a compound of claim 2.

18. A method of retarding senescence in soybean plants which comprises applying to the plant a plant regulating amount of the isomeric mixture of claim 3.

19. A method of retarding senescence in soybean plants which comprises applying to the plant a plant regulating amount of the compound of claim 6.

20. A method of retarding senescence in soybean plants which comprises applying to the plant a plant regulating amount of the compound of claim 7.

21. A method of retarding senescence in soybean plants which comprises applying to the plant a plant regulating amount of the compound of claim 9.

22. A method of retarding senescence in soybean plants which comprises applying to the plant a plant regulating amount of the isomeric mixture of claim 11.

23. A method of retarding senescence in soybean plants which comprises applying to the plant a plant regulating amount of the isomeric mixture of claim 12.

24. A method of retarding senescence in soybean plants which comprises applying to the plant a plant regulating amount of the isomeric mixture of claim 13.

* * * * *

UNITED STATES PATENT AND TRADEMARK OFFICE
CERTIFICATE OF CORRECTION

PATENT NO. : 4,735,650

DATED : April 5, 1988

INVENTOR(S) : Robert N. Henrie, II

It is certified that error appears in the above-identified patent and that said Letters Patent is hereby corrected as shown below:

Column 1, line 50, "halogen" should read --hydrogen; line 64, "senescenece" should read --senescence--. Column 2, line 25, "Bull," should read --Bull.--. Column 5, line 22, "washed" should read --washes--; line 49, "7.01" should read --7.0--. Column 6, line 68, "The reaction" should be deleted. Column 7, line 1, "mixture was concentrated for three days." should be deleted. Column 10, line 28, "Attapulite" should read --Attapulgite--; line 36, "4.00" should read --1.00--; line 37, --4.00-- should appear in the % by Wt. column. Column 15, line 28, "1." should read --1.2--; Column 16, line 18, insertion in heading "Days Senescence Compared to the Untreated check" should read --Days Senescence Delayed as Compared to the Untreated Check--.

Signed and Sealed this

Eighth Day of November, 1988

Attest:

DONALD J. QUIGG

Attesting Officer

Commissioner of Patents and Trademarks